(12) United States Patent
Horton, III

(10) Patent No.: US 6,766,097 B2
(45) Date of Patent: Jul. 20, 2004

(54) UV PORTAL-BASED APPLIANCES AND CONTAINERS

(75) Inventor: Isaac B. Horton, III, Raleigh, NC (US)

(73) Assignee: Remote Light, Inc., Raleigh, NC (US)

( * ) Notice: Subject to any disclaimer, the term of this patent is extended or adjusted under 35 U.S.C. 154(b) by 42 days.

(21) Appl. No.: 10/007,534

(22) Filed: Nov. 9, 2001

(65) Prior Publication Data

US 2002/0063954 A1 May 30, 2002

Related U.S. Application Data

(63) Continuation-in-part of application No. 09/724,180, filed on Nov. 28, 2000, now Pat. No. 6,524,529.

(51) Int. Cl.[7] .................................................. A61L 2/00
(52) U.S. Cl. ........................ 385/147; 210/636; 210/748; 422/24; 250/454.11
(58) Field of Search ................................ 250/365, 373, 250/455.11, 432 R, 65, 454.11; 385/147; 210/636, 748, 192; 422/22–24; 359/350

(56) References Cited

U.S. PATENT DOCUMENTS

| | | | |
|---|---|---|---|
| 3,589,862 A | * | 6/1971 | Veloz ........................ 422/24 X |
| 4,102,645 A | * | 7/1978 | Meacham, Jr. et al. . 250/432 R |
| 4,103,167 A | * | 7/1978 | Ellner ..................... 250/432 R |
| 4,337,119 A | * | 6/1982 | Donahue ..................... 196/46 |
| 4,755,292 A | * | 7/1988 | Merriam ............. 250/432 R X |
| 4,757,426 A | * | 7/1988 | Scheller et al. ............... 362/20 |
| 5,207,576 A | * | 5/1993 | Vassiliadis et al. ......... 433/215 |
| 6,042,720 A | * | 3/2000 | Reber et al. .............. 422/22 X |
| 6,094,767 A | * | 8/2000 | Iimura ...................... 422/22 X |
| 6,216,918 B1 | * | 4/2001 | Saveliev et al. .......... 422/24 X |
| 6,409,928 B1 | * | 6/2002 | Gonzalez et al. ......... 422/24 X |

* cited by examiner

Primary Examiner—Jay Patidar
(74) Attorney, Agent, or Firm—Glasgow Law Firm, PLLC

(57) ABSTRACT

A portal-based system for ultraviolet disinfection (UV) of containers and appliances, the system including a container with a housing having at least one portal for receiving UV light input for transmission into the container. The portal is designed such that a fiber optic transmission line is removably connectable to it. This system may include at least one portal optical component positioned between the portal and the interior of the appliance, thereby producing an enhanced sterilization of microorganisms within the container and/or appliance.

31 Claims, 2 Drawing Sheets

UV PORTAL-BASED APPLIANCES AND CONTAINERS

This nonprovisional utility patent application claims the benefit of one or more prior filed copending nonprovisional applications; the present application is a Continuation-In-Part of application Ser. No. 09/724,180, filed Nov. 28, 2000, now U.S. Pat. No. 6,524,529 which is incorporated herein by reference in its entirety.

BACKGROUND OF THE INVENTION

1. Field of the Invention

The present invention relates generally to a system and method for ultraviolet disinfection and, more particularly, to a system and method for ultraviolet disinfection of appliances.

2. Description of the Prior Art
UV Mechanism of Action

It is well known in the art to use ultraviolet light (UV) for the microbial disinfection of liquids and surfaces. Ultraviolet light, at the germicidal wavelength of 253.7 nanometers, alters the genetic (DNA) material in cells so that bacteria, viruses, molds, algae and other microorganisms can no longer reproduce. The microorganisms are considered dead, and the risk of disease from them is eliminated. As the UV lamps irradiate a fluid or surface in UV disinfection systems, the microorganisms are exposed to a lethal dose of UV energy. UV dose is measured as the product of UV light intensity times the exposure time within the UV lamp array. Microbiologists have determined the effective dose of UV energy to be approximately about 34,000 microwatt-seconds/cm2 needed to destroy pathogens as well as indicator organisms found in wastewater. Typical prior art disinfection systems and devices emit UV light at approximately 254 nm, which penetrates the outer cell membrane of microorganisms, passes through the cell body, reaches the DNA and alters the genetic material of the microorganism, destroying it without chemicals by rendering it unable to reproduce.

Ultraviolet light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of bacteria, viruses and other pathogens and thus destroys their ability to multiply and cause disease, effectively resulting in sterilization of the microorganisms. Specifically, UV "C" light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 260 nm provides the highest germicidal effectiveness. While susceptibility to UV light varies, exposure to UV energy for about 20 to about 34 milliwatt-seconds/cm2 is adequate to deactivate approximately 99 percent of the pathogens.

Regulation of Drinking Water Standards

Exposure to pathogens does not always cause disease; whether drinking contaminated water could produce disease depends on the type and quantity of pathogen ingested and the health (nutritional and immunological) status of the person ingesting the pathogen. However, the use of low-level antibiotics to improve feed conversion in domestic animals has led to the emergence of antibiotic-resistant pathogens. In recognition of this problem, U.S. governmental agencies are seeking to improve the control of food production through such programs as the Hazard Analysis Critical Control Point (HACCP).

Traditionally, the most common means of maintaining water used in household appliances at an acceptable purity for long periods of time is through the addition of reactive chlorine. Unfortunately, certain microorganisms, such as Cryptosporidium, have developed resistance to reactive chlorine, and have now returned as a public health problem. Additionally, dumping of contaminated waste such that a municipal water treatment facility is overtaxed has resulted in ineffective water purification with the result that pathogens are delivered to humans in the drinking water. Although persons might prevent such contamination through the use of purified drinking water, other appliances that use municipal water may be contaminated with the pathogens and consequently expose the user to the pathogen. Thus a need exists for appliances and other devices whose contact surfaces and/or interior contents can be easily sterilized.

A system for UV light treatment of appliances has been described by the inventor in U.S. patent application Ser. No. 09/724,180. This system includes transmission of UV light to appliances via fiber optic transmission lines for the purpose of microbial disinfection. However, no appliances or storage devices are currently equipped with a portal for connection to a fiber optic transmission line for the purpose of UV sterilization.

Thus, there remains a need for appliances and container devices that contain a portal to which a fiber optic transmission line can be attached for the purpose of UV sterilization.

SUMMARY OF THE INVENTION

The present invention is directed to a portal system for appliances and containers for the attachment of a fiber optic transmission line for the purpose of UV sterilization. One object of the present invention is to provide a portal-based appliance system for ultraviolet disinfection (UW) incorporated within appliances for providing disinfection along with the appliance function, the system including at least one portal for receiving UV light input into the appliance from a UV light source.

Another object of the present invention is to provide a portal system for ultraviolet (UV) disinfection of containers that includes at least one portal included as part of the container housing for providing disinfection within the container.

Accordingly, one aspect of the present invention is to provide a portal-based appliance system for ultraviolet disinfection (UV) of appliances, wherein the system includes an appliance having at least one portal for receiving UV light input.

Another aspect of the present invention is to provide a portal system for ultraviolet disinfection (UV) of containers, wherein the system includes at least one portal included with the container housing for receiving UV light input into the container from a UV light source.

These and other aspects of the present invention will become apparent to those skilled in the art after a reading of the following description of the preferred embodiment according to the present invention when considered with the drawings.

DETAILED DESCRIPTION OF THE PREFERRED EMBODIMENTS

Figure 1:
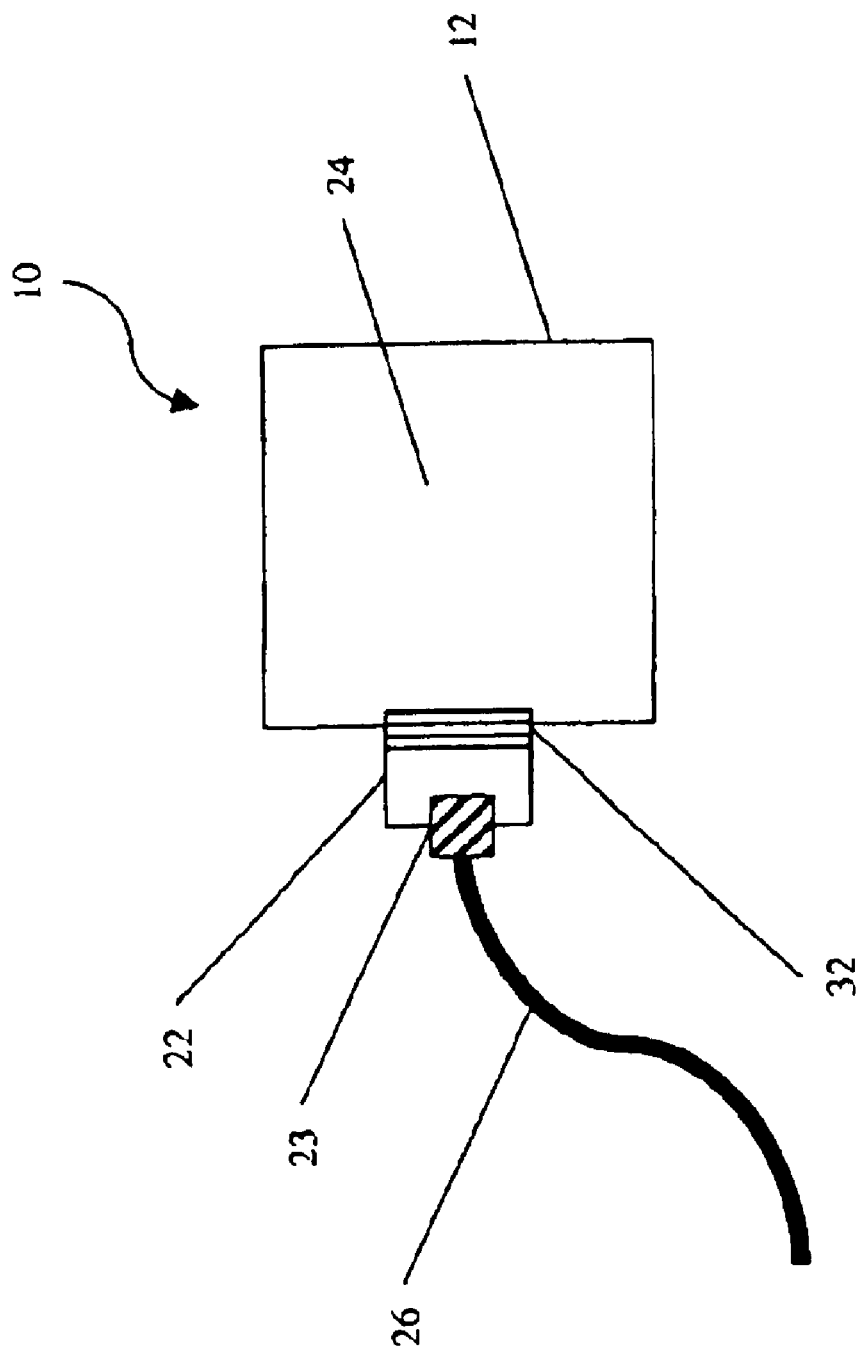
FIG. 1 is a schematic diagram of the complete UV appliance portal system.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Figure 2:
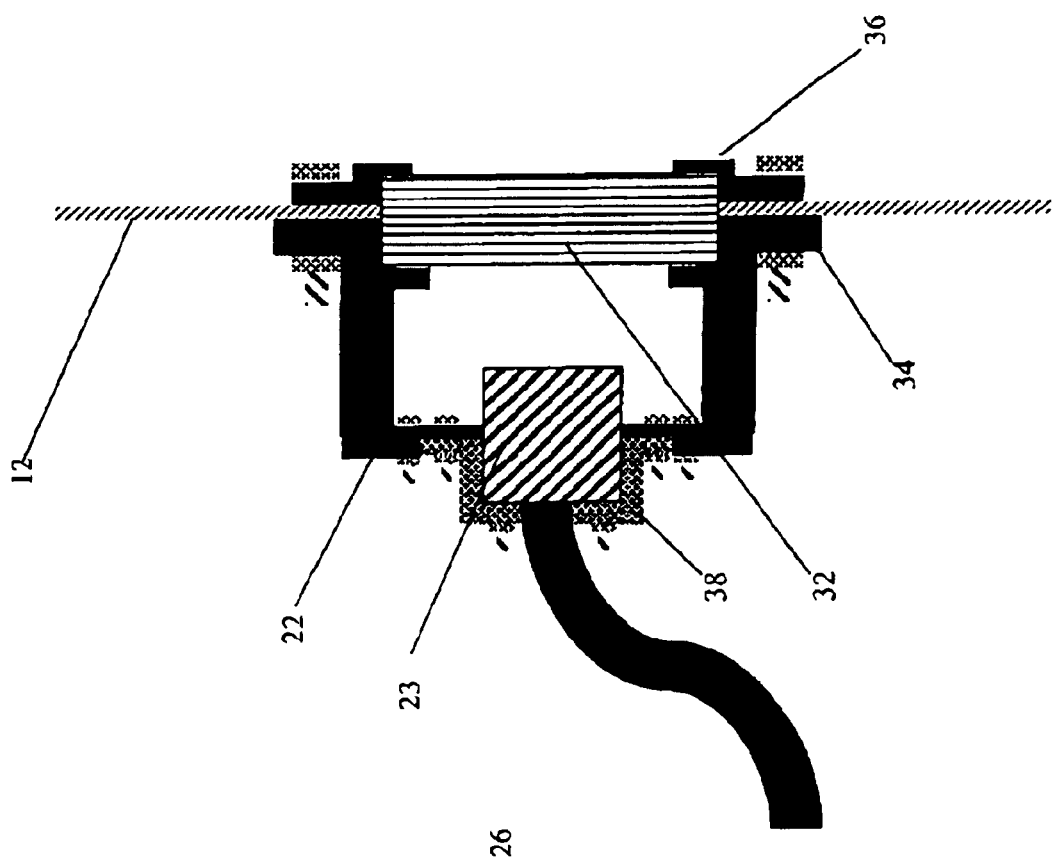
FIG. 2 is a close-up view of the portal show in FIG. 1.

Referring now to the drawings in general, the illustrations are for the purpose of describing a preferred embodiment of the invention and are not intended to limit the invention thereto. FIG. 1 shows a schematic diagram of a UV appliance or container portal system, generally described as 10. In the preferred embodiment, an appliance or container 24 is equipped with a portal 22, which may alternatively be at least one portal if more than one light input is desired, thus allowing at least one fiber optic transmission line 26 to provide UV light to the appliance. The at least one portal may include a respective fiber optic transmission line fastener 23, to removably secure the fiber optic transmission line(s) to the device. The portal is equipped with an interface device 32 that controls the interface between the portal and the interior of the appliance or container. The interface device ensures the security of the internal compartment of the appliance or container and/or prevents the escape of the interior contents of the appliance or container via the at least one portal. Preferably, the interface device is UV transmissive, such that UV light may pass through it. More preferably, the interface device is an interface optical device or devices. These interface optical devices, or portal optics, control and direct the UV light in order to enhance the disinfection of the appliance or container interior 24. Alternately, when the appliance is not being disinfected, the interface device is not necessarily UV transmissive, but may be engineered and constructed of materials such that it can preserve the security of or prevent the escape of the internal contents and components of the appliance. FIG. 2 includes an example embodiment of a portal mounting mechanism 34 for mounting the portal 22 to the appliance 12 integrated with an interface mounting mechanism 36 for mounting the interface 32 to the appliance 12. FIG. 2 also shows a fiber optic transmission line fastener mounting mechanism 38 for mounting a fiber optic transmission line fastener 23 to the portal 22. The mounting mechanisms in this example embodiment include brackets with bolted fittings for securably attaching the components to the appliance.

Additionally, the portal optics may contain a photocatalyst that degrades compounds contacting the surface of the portal optics. For example, photoactivated semiconductors may be incorporated into the optics that interface with the interior of the appliance. The photocatalyst may include photo-activated semiconductors such as Titanium Oxide; TiO2 (photo activation wavelength; not more than 388 nm), Tungsten Oxide; WO2 (photo activation wavelength; not more than 388 um), Zinc Oxide; ZnO (photo activation wavelength; not more than 388 nm), Zinc Sulfide; ZnS (photo activation wavelength; not more than 344 um) and Tin Oxide; SnO2 (photo activation wavelength; not more than 326 nm). In addition to these catalysts, other catalysts, such as PtTiO$_2$, are known. TiO2 may be preferably applied as the photocatalyst, considering that the activation power is very high, the catalyst is long-lived with high durability, and safety for human applications is certified, as TiO2 has been used safely for a long time in cosmetic and food applications. When such a surface is irradiated with activating light, fatty acids and other organic chemicals are chemically reduced, resulting in degradation to smaller volatile products such as methane, ethane, etc. Thus, the incorporation of TiO$_2$ or other photocatalytic material into the portal optics with subsequent irradiation by activating wavelengths reduces the fouling of the portal optics, thus extending the time between required maintenance and/or replacement of the optics.

Advantageously, the use of optical components enables the system to maximize the intensity, focus, and control of the UV light rays at the output for any given UV light source or lamp in order to enhance the UV disinfection capacity of the system. Optical components may include, but are not limited to, reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920, which are commonly owned by the assignee of the present invention, and which are incorporated herein by reference in their entirety. Additionally, optical component such as gratings, dichroic filters, focalizers, gradient lenses, gradient reflectors, off-axis lenses, and off-axis reflectors may be used. All UV transmissive optical components are made of UV-transmissive material and all UV-reflective optical components are made of UV-reflective material. These optics may extend into the appliance. For example, fiber optic transmission lines may be used to route UV light to the various areas of the appliance. The fiber optic lines may include glass fibers, acrylic fibers, liquid core fibers, core sheath fibers, or a combination of fibers.

A wide range of applications are contemplated within the scope of the present invention, including application of the UV fluid disinfectant system and method to appliances and containers involved in washing, rinsing, storing, fluid dispensing, and combinations thereof. By way of example, the disinfection of appliances, includes, but is not limited to, ambient temperature and chilled water tanks, refrigerators, water fountains, water towers, beverage makers, beverage dispensers, dishwashers, water heaters, washing machines, bathtubs, showers, toilets, and water pumps. These appliances may be for commercial or household use. Additionally, appliances not normally associated with food consumption, but that can harbor pathogens, may be fitted with a UV disinfectant system and method according to the present invention. By way of example and not of limitation, vacuum cleaners, air conditioners, toilet flush reservoirs, waste receptacles, animal housing devices, biomedical storage containers, ion-exchange columns, aquariums, nuclear fluid storage devices, and cabinets, bins, and other storage containers and the like may be fitted with a UV disinfection system and method according to the present invention in order to disinfect or maintain the microbial purity of the appliance or the emissions therefrom.

Containers can be bulk-type containers, such as storage bins, cabinets, toilet flush reservoirs, and the like, and can also be individual-use containers, such as beverage containers for water, milk, coffee, tea, juice, wine, beer, carbonated beverages, and the like, or biological fluid containers, such as for blood and blood products, fermentation products, cell culture products, biotechnology products, and the like.

These multiple applications may also be connected to a single light source, such as a light pump, by light guides. Such an arrangement would eliminate the need for a lamp or light source at every point of application. Because it may not be necessary to continuously irradiate each point of application, such an arrangement would allow the same size lamp as would be require for a single application to service multiple applications intermittently and/or on demand, thus utilizing the lamp more efficiently. Additionally, placing the lamp exterior to the tank reduces the risk of glass and/or mercury contaminating the appliance should the lamp or lamp housing break. An additional benefit to such a configuration is that filters previously required in immersion-type systems to prevent such contamination are no longer required.

Certain modifications and improvements will occur to those skilled in the art upon a reading of the foregoing description. By way of example, various optical components are used depending upon the particular UV light source or lamp selection for a given system.

All modifications and improvements have been deleted herein for the sake of conciseness and readability but are properly within the scope of the following claims.

I claim:

1. A portal-based appliance system for ultraviolet disinfection (UV) of interior surfaces and contents of containers, the system comprising the container having a housing with at least one portal positioned on the housing of the container for receiving UV light input into the container from a UV light source, the portal further including an interface device having at least one interface optical device for controlling and directing the UV light to provide a focused, controlled light output in order to enhance the disinfection of the appliance or container interior for sterilizing the interior surfaces and contents of the container.

2. The UV system according to claim 1, wherein the portal is connectable to fiber optic transmission lines.

3. The UV system according to claim 2, wherein the portal is a fiber optic transmission line-ready portal.

4. The UV system according to claim 3, wherein the fiber optic transmission line-ready portal includes a fiber optic transmission line fastener.

5. The UV system according to claim 1, wherein the interface device further provides for protection to appliance components.

6. The UV system according to claim 5, wherein the interface device is UV-transmissive.

7. The UV system according to claim 1, wherein the container is used for animal housing.

8. The UV system according to claim 1, further including at least one portal optical component positioned between the portal opening and the interior of the appliance.

9. The UV system according to claim 8, wherein the at least one portal optical component is UV transmissive.

10. The UV system according to claim 8, wherein the at least one portal optical component is UV reflective.

11. The UV system according to claim 8, wherein the at least one portal optical component is selected from the group consisting of reflectors, shutters, lenses, splitters, focalizers, mirrors, rigid and flexible light guides, homogenizer, mixing rods, manifolds, couplers, filters, gratings, diffracters, color wheels, and combinations thereof.

12. The UV system according to claim 8, wherein the at least one portal optical component includes at least one photocatalyst that degrades compounds contacting the surface of the portal optic.

13. The UV system according to claim 12, wherein the at least one photocatalyst is selected from the group consisting of TiO2, WO2, ZnO, ZnS, SnO2, and $PtTiO_2$ and the like.

14. The UV system according to claim 1, wherein the container is an appliance selected from the group consisting of fluid-treatment appliances, fluid-dispensing appliances, fluid-storage appliances, fluid-manufacturing appliances, and combinations thereof.

15. The UV system according to claim 1, wherein the container is an individual use container.

16. The UV system according to claim 15, wherein the container is a beverage container.

17. The UV system according to claim 16, wherein the beverage container is selected from the group consisting of water, coffee, tea, milk, juice, carbonated beverage, wine, beer, and combinations thereof.

18. The UV system according to claim 15, wherein the container is a biological fluid container.

19. The UV system according to claim 18, wherein the container is used to contain blood, blood products, fermentation products, cell culture products, biotechnology products, and combinations thereof.

20. A portal system for ultraviolet disinfection (UV) of appliances, the system comprising at least one portal for receiving UV light input, the at least one portal further including a corresponding at least one interface device having at least one interface optical device for controlling and directing the UV light input to provide a focused controlled light output in order to enhance the disinfection of the appliance interior for sterilizing the interior surfaces and contents of the appliances.

21. The UV system according to claim 20, wherein the portal is connectable to fiber optic transmission lines.

22. The UV system according to claim 21, wherein the portal is a fiber optic transmission line-ready portal.

23. The UV system according to claim 22, wherein the fiber optic transmission line-ready portal includes a fiber optic transmission line fastener.

24. The UV system according to claim 20, wherein the portal includes an interface device for providing protection to appliance components.

25. The UV system according to claim 24, wherein the interface device is UV-transmissive.

26. The UV system according to claim 20, further including at least one portal optical component positioned between the portal opening and the interior of the appliance.

27. The UV system according to claim 26, wherein the at least one portal optical component is UV transmissive.

28. The UV system according to claim 26, wherein the at least one portal optical component is UV reflective.

29. The UV system according to claim 26, wherein the at least one portal optical component is selected from the group consisting of reflectors, shutters, lenses, splitters, focalizers, mirrors, rigid and flexible light guides, homogenizer, mixing rods, manifolds, couplers, filters, gratings, diffracters, color wheels, and combinations thereof.

30. The UV system according to claim 26, wherein the at least one portal optical component includes at least one photocatalyst that degrades compounds contacting the surface of the portal optic.

31. The UV system according to claim 30, wherein the at least one photocatalyst is selected from the group consisting of TiO2, WO2, ZnO, ZnS, SnO2, and $PtTiO_2$ and the like.

* * * * *